United States Patent [19]

Walser

[11] 4,259,241
[45] Mar. 31, 1981

[54] PROCESS FOR THE PREPARATION OF IMIDAZOBENZODIAZEPINES

[75] Inventor: Armin Walser, West Caldwell, N.J.

[73] Assignee: Hoffmann-La Roche Inc., Nutley, N.J.

[21] Appl. No.: 123,318

[22] Filed: Feb. 21, 1980

Related U.S. Application Data

[62] Division of Ser. No. 43,417, May 29, 1979, Pat. No. 4,226,768.

[51] Int. Cl.³ ............................................ C07D 487/04
[52] U.S. Cl. .............................. 260/243.3; 260/245.6; 260/245.7
[58] Field of Search .......................... 260/245.6, 243.3

[56]  References Cited
U.S. PATENT DOCUMENTS 4,125,726  11/1978  Walser .............................. 260/245.6

Primary Examiner—Alton D. Rollins
Attorney, Agent, or Firm—Jon S. Saxe; Bernard S. Leon; Frank P. Hoffman

[57]  ABSTRACT

A multistep process is presented for the preparation of imidazobenzodiazepines of the formula

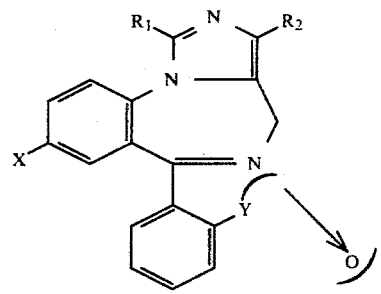

wherein X is selected from the group consisting of hydrogen, halogen, nitro and trifluoromethyl; Y is selected from the group consisting of hydrogen, halogen or trifluoromethyl; $R_1$ is hydrogen or lower alkyl and $R_2$ is a disubstituted amine.

Also presented are novel intermediates utilized in the process.

The end products and intermediates are useful as sedatives, anxiolytics, muscle relaxants and anticonvulsants.

The end products are especially useful in intravenous compositions for use in preoperative anesthesia.

1 Claim, No Drawings

PROCESS FOR THE PREPARATION OF IMIDAZOBENZODIAZEPINES

This is a division, of application Ser. No. 043,417, filed May 29, 1979, now U.S. Pat. No. 4,226,768.

DESCRIPTION OF THE INVENTION

The present invention relates to a process to produce imidazobenzodiazepines of the formula

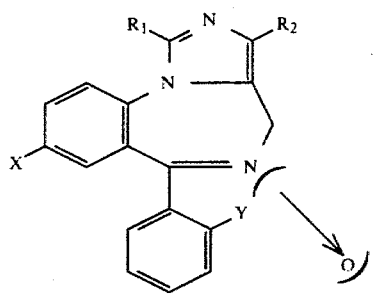

wherein X is selected from the group consisting of hydrogen, halogen, nitro and trifluoromethyl; Y is selected from the group consisting of hydrogen, halogen or trifluoromethyl; $R_1$ is hydrogen or lower alkyl and $R_2$ is a disubstituted amine The imidazobenzodiazepines are useful as sedatives, anxiolytics, muscle relaxants and anticonvulsants, a description of these compounds can be found in Belgian Pat. No. 839,364 which is incorporated herein by reference.

As utilized in the present specification, the terms "halo" or "halogen" mean all four forms thereof, i.e., chlorine, bromine, iodine and fluorine, except where otherwise indicated.

As used in this disclosure, the term "lower alkyl" or "alkyl" comprehends both straight and branched chain ($C_1$ to $C_7$) carbon-hydroxy radicals, preferably $C_1$ to $C_4$ carbon-hydroxy radicals, such as, methyl, ethyl, propyl, isopropyl, butyl and the like.

By the term "disubstituted amino" is meant a nitrogen atom substituted by lower alkyl or aralkyl, e.g., benzyl. Also within the ambit of the term "disubstituted amino" is a cyclic moiety wherein the dialkyl substituents are combined with the nitrogen atom and another heteroatom, e.g., oxygen to form a cyclic group, e.g., morpholino.

The following reaction scheme sets forth the novel process.

Reaction Scheme

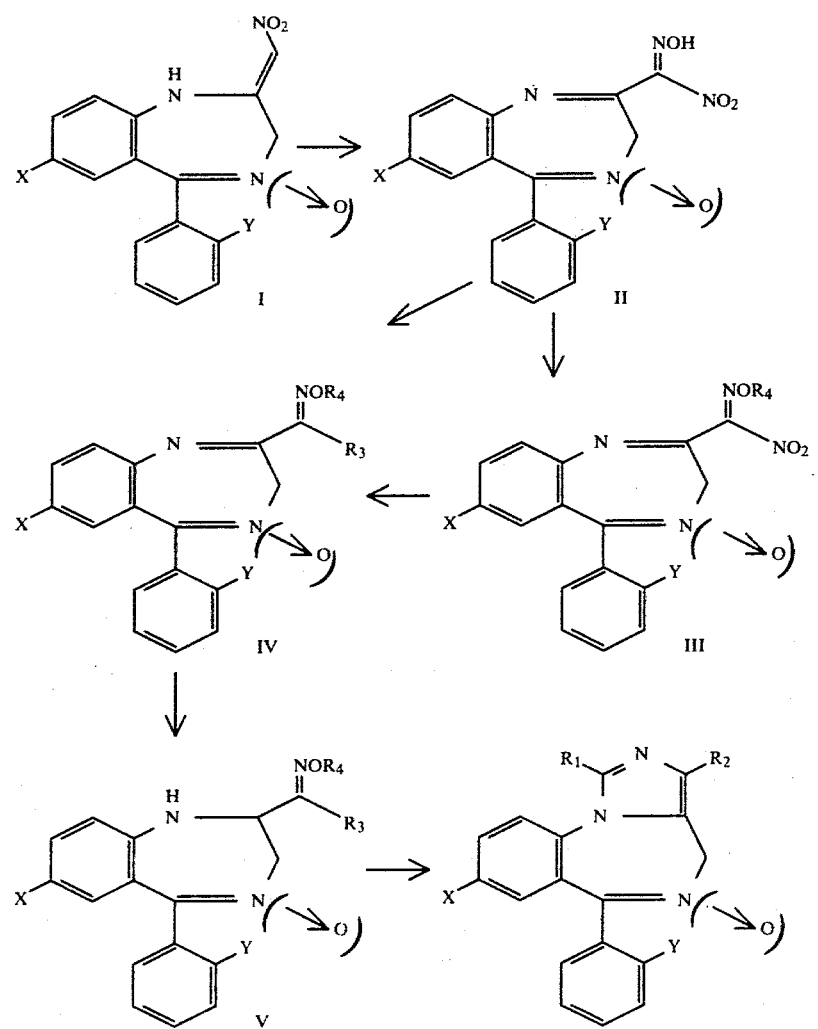

wherein X is selected from the group consisting of hydrogen, halogen, nitro and trifluoromethyl; Y is selected from the group consisting of hydrogen, halogen or trifluoromethyl; $R_1$ is hydrogen or lower alkyl, $R_2$ is a disubstituted amine and $R_3$ is an amino or substituted amino $R_4$ is lower alkyl or hydrogen.

I→II

The nitromethylene compound of formula I is a known compound. Methods for its preparation are described in the previously mentioned Belgian Pat. No. 839,364. This starting material is thereafter reacted with a nitrosating agent, such as, nitrosyl chloride or nitrous acid which is generated from sodium or potassium nitrite in an acetic acid solvent. As a solvent, acetic acid is preferred but mixtures of acetic acid and a $C_1$ to $C_4$ alcohol or water may also be utilized. The reaction temperature may range from about 0° C. to 50° C. with about room temperature as preferred.

II→III

The compound of formula II is thereafter alkylated by reaction with a diazoalkane, such as, diazomethane or diazoethane in a wide range of solvents, such as, inert hydrocarbons or chlorinated hydrocarbons, e.g., benzene, toluene, chloroform and methylene chloride or ethers, such as, tetrahydrofuran. The temperature of the reaction may range from about −50° C. to +50° C. with about room temperature as preferred.

III→IV or II→IV

The compounds of formulas III or II may thereafter undergo a nucleophilic displacement of the nitro group with an amine nucleophile. Suitable nucleophiles include ammonia, primary and secondary amines or alkali metal salts of primary and secondary amines. Examples of the above include monoalkylamines such as monomethylamine and monoethylamine, dialkylamines such as diethylamine, aromatic primary and secondary amines such as aniline and monomethyl-aniline, cyclic amines such as morpholine, piperidine and pyrrolidine, functionalized derivatives of the above amines such as 2-hydroxyethylamine (ethanolamine), 2-aminoethylamine (ethylenediamine), carbalkoxymethylamine, glycine esters.

A variety of solvents may be utilized, such as, inert hydrocarbons or chlorinated hydrocarbons, e.g., benzene, toluene, chloroform or methylene chloride or ethers, such as, tetrahydrofuran. An excess of the particular amine chosen is utilized in the reaction. The reaction temperature may range from about 0° C. to 100° C. with room temperature as preferred.

IV→V

The compound of formula IV is thereafter reduced by reaction with sodium borohydride. A variety of solvents may be utilized, such as, $C_1$-$C_4$ alcohols or mixtures with inert hydrocarbons or chlorinated hydrocarbons, e.g., benzene, toluene, chloroform or methylene chloride, ethers or dimethylformamide. Preferred is a mixture of ethanol and tetrahydrofuran. The reaction temperature varies from about 0° C. to 50° C. with room temperature as preferred.

V→VI

The compound of formula V where $R_3$ is amino, dialkylamine or a cyclic amine may be cyclized to the desired imidazobenzodiazepines of formula VI by condensation with an aliphatic or aromatic aldehyde, e.g., acetaldehyde, in the presence of an acid catalyst, such as, p-toluene sulfonic acid or hydrochloric or sulfuric acid. Suitable solvents include $C_1$ to $C_4$ alcohols, inert hydrocarbons and chlorinated hydrocarbons as mentioned earlier, high boiling ethers, acetic acid and propronic acid. The reaction temperature may vary from about room temperature to 120° C. with the boiling point of the chosen solvent as preferred.

The compounds of formulas II, III, IV and V are novel intermediates in the present process and also exhibit activity as sedatives and anxiolytics.

EXAMPLE 1

7-Chloro-5-(2-fluorophenyl)-N-methoxy-α-nitro-3H-1,4-benzodiazepine-2-methanimine A solution of diazomethane in ether was added to a suspension of 6 g (0.0163 mole) of 7-chloro-5-(2-fluorophenyl)-N-hydroxy-α-nitro-3H-1,4-benzodiazepine-2-methanimine in 100 ml of tetrahydrofuran. After sitting at room temperature for 1 hr the excess diazomethane was destroyed by addition of glacial acetic acid. The solvent was evaporated under reduced pressure and the residue was passed over 100 g of silica gel using methylene chloride. Crystallization from ether/hexane gave light yellow crystals with mp 130°–133° C.

EXAMPLE 2

7-Chloro-5-(2-fluorophenyl)-3H-1,4-benzodiazepine-2-N'-hydroxycarboximidamide

A mixture of 7.2 g (0.02 mole) of 7-chloro-5-(2-fluorophenyl)-N-hydroxy-α-nitro-3H-1,4-benzodiazepine-2-methanimine and 50 ml of ethanol containing 20% (v/v) of ammonia was allowed to sit at room temperature overnight. The precipitated crystals were collected, washed with methanol, 2-propanol and ether to leave end product. The analytical sample was recrystallized from tetrahydrofuran/ethanol to give yellowish crystals with mp 248°–249° C.

EXAMPLE 3

7-Chloro-5-(2-fluorophenyl)-3H-1,4-benzodiazepine-2-N'-hydroxycarboximidamine 4-oxide A mixture of 1 g (2.65 mmole) of 7-chloro-5-(2-fluorophenyl)-N-hydroxy-α-nitro-3H-1,4-benzodiazepine-2-methanimine 4-oxide and 20 ml of methanol containing 20% (v/v) of ammonia was allowed to sit overnight. The precipitated crystals were collected, washed with methanol, water and methanol to yield end product with mp 252°–254° C. dec. For analysis it was recrystallized from methanol/ethanol/tetrahydrofuran to give yellow crystals with mp 258°–260° C.

EXAMPLE 4

7-Chloro-5-(2-fluorophenyl)-3H-1,4-benzodiazepine-2-N'-hydroxy-N-methylcarboximidamide A solution of 3.6 g (0.01 mole) of 7-chloro-5-(2-fluorophenyl)-N-hydroxy-αnitro-3H-1,4-benzodiazepine-2-methanimine in 50 ml ethanol containing 20% (v/v) of methylamine was allowed to sit at room temperature overnight. The solvents were evaporated under reduced pressure and the residue was partitioned between methylene chloride and water. The organic phase was dried and evaporated and the residue was crystallized from ether to give yellowish crystals. The analyticl sample was recrystallized from methylene chloride/ethyl acetate/hexane, mp 223°–225° C. dec.

EXAMPLE 5

7-Chloro-5-(2-fluorophenyl)-3H-1,4-benzodiazepine-2-N'-hydroxy-N,N-dimethylcarboximidamide Reaction of 7-chloro-5-(2-fluorophenyl)-N-hydroxy-α-nitro-3H-1,4-benzodiazepine-2-methanimine, 7.2 g (0.02 mole), with dimethylamine in tetrahydrofuran yielded product which was recrystallized from methanol/ethyl acetate for analysis, mp 160°–164° C.

EXAMPLE 6

7-Chloro-5-(2-fluorophenyl)-3H-1,4-benzodiazepine-2-N'-hydroxy-N,N-dimethylcarboximidamide 4-oxide A solution of dimethylamine in tetrahydrofuran, 50 ml, (20%, v/v) was added to a suspension of 7.5 g (0.02 mole) of 7-chloro-5-(2-fluorophenyl)-N-hydroxy-α-nitro-3H-1,4-benzodiazepine-2-methanimine in 50 ml of tetrahydrofuran. After sitting at room temperature overnight, the mixture was evaporated under reduced pressure and the residue was partitioned between methylene chloride and saturated aqueous sodium bicarbonate solution. The organic phase was dried and evaporated and the residue was crystallized from ethyl acetate to yield end product as crystals. The analytical sample was recrystallized from methanol/ethyl acetate, mp 190°–192° C. dec.

EXAMPLE 7

[7-Chloro-5-(2-fluorophenyl)-3H-1,4-benzodiazepin-2-yl](4-methyl-1-piperazinyl)methanone oxime This compound was obtained by reacting 7-chloro-5-(2-fluorophenyl)-N-hydroxy-α-nitro-3H-1,4-benzodiazepine-2-methanimine with N-methylpiperazine in tetrahydrofuran. The analytical sample was recrystallized from ethanol, mp 198°–200° C.

EXAMPLE 8

[7-Chloro-5-(2-fluorophenyl)-4-oxide-3H-1,4-benzodiazepin-2-yl](4-methyl-1-piperazinyl)-methanone oxime Reaction of 7-chloro-5-(2-fluorophenyl)-N-hydroxy-α-nitro-3H-1,4-benzodiazepine-2-methanimine with N-methylpiperazine in tetrahydrofuran gave this compound as yellow crystals. For analysis it was recrystallized from ethanol, mp 184°–186° C. dec.

EXAMPLE 9

7-Chloro-5-(2-fluorophenyl)-2-[1-[(hydroxyimino)methyl]pyrrolidinyl]-3H-1,4-benzodiazepine Reaction of 7-chloro-5-(2-fluorophenyl)-N-hydroxy-α-nitro-3H-1,4-benzodiazepine-2-methanimine with pyrrolidine in tetrahydrofuran overnight at room temperature yielded yellowish crystals. For analysis a sample was recrystallized from tetrahydrofuran/ethanol, mp 175°–178° C.

EXAMPLE 10

7-Chloro-5-(2-fluorophenyl)-2-[1-[(hydroxyimino)methyl]pyrrolidinyl]-3-H-1,4-benzodiazepine 4-oxide This compound was obtained by reacting 7-chloro-5-(2-fluorophenyl)-N-hydroxy-α-nitro-3H-1,4-benzodiazepine-2-methanone with pyrrolidine in tetrahydrofuran. The product was crystallized from ethyl acetate/ether and recrystallized for analysis from methanol/ethyl acetate, mp 168°–172° C.

EXAMPLE 11

7-Chloro-5-(2-fluorophenyl)-2-[4-[(hydroxyimino)methyl]morpholinyl]-3H-1,4-benzodiazepine Morpholine, 5 ml, was added to a suspension of 5 g of 7-chloro-5-(2-fluorophenyl)-N-hydroxy-α-nitro-3H-1,4-benzodiazepine-2-methanimine in 75 ml of tetrahydrofuran. After standing at room temperature for 6 hours the reaction mixture was filtered and the filtrate was evaporated. The residue was partitioned between methylene chloride and sodium bicarbonate solution. The organic phase was dried and evaporated and the residue was crystallized from ether to yield end product as yellow crystals. The analytical sample was recrystallized from methanol/ethyl acetate, mp 191°–193° C. dec.

EXAMPLE 12

7-Chloro-5-(2-fluorophenyl)-2-[4-[(hydroxyimino)methyl]morpholinyl]-3H-1,4-benzodiazepine 4-oxide Reaction of 7-chloro-5-(2-fluorophenyl)-N-hydroxy-α-nitro-3H-1,4-benzodiazepine-2-methanimine with a solution of morpholine in tetrahyrofuran gave similarly 7-chloro-5-(2-fluorophenyl)-2-[4-[(hydroxyimino)methyl]morpholinyl]-3H-1,4-benzodiazepine 4-oxide. It was crystallized from ethyl acetate and recrystallized for analysis from a mixture of methanol/tetrahydrofuran/ethyl acetate to give yellow crystals with mp 211°–213° C. dec.

EXAMPLE 13

7-Chloro-5-(2-fluorophenyl)-N'-methoxy-3H-1,4-benzodiazepine-2-carboximidamide

A mixture of 1.5 g (0.004 mole) of 7-chloro-5-(2-fluorophenyl)-N-methoxy-α-nitro-3H-1,4-benzodiazepine-2-methanimine and 20 ml of methanol containing 20% (v/v) of ammonia was allowed to sit at room temperature for 4½ hours. After partial evaporation residue was partitioned between methylene chloride and saturated aqueous sodium bicarbonate solution. The methylene chloride layer was dried and evaporated. The residue was passed over neutral alumina using ether. Crystallization of the combined eluates from ether/hexane gave end product as colorless crystals with mp 120°–124° C.

EXAMPLE 14

7-Chloro-5-(2-fluorophenyl)-N-methyl-N'-methoxy-3H-1,4-benzodiazepine-2-carboximidamide Reaction of 0.5 g of 7-chloro-5-(2-fluorophenyl)-N-methoxy-α-nitro-3H-1,4-benzodiazepine-2-methanimine with methylamine in ethanol (20% v/v) gave the same workup and purification procedure colorless product, crystallized from ether/hexane; mp 140°–142° C.

EXAMPLE 15

7-Chloro-5-(2-fluorophenyl)-2,3-dihydro-1H-1,4-benzodiazepine-2-N'-hydroxy-carboximidamide 7-chloro-5-(2-fluorophenyl)-3H-1,4-benzodiazepine-2-N'-hydroxycarboximidamide, 5 g or 0.015 mole, was dissolved by warming in a mixture of 250 ml of ethanol and 100 ml of tetrahydrofuran. Sodium borohydride, 2 g (0.053 mole) was added at room temperature and the mixture was stirred overnight. The solvents were evaporated partially under reduced pressure and the residue was partitioned between methylene chloride and saturated aqueous sodium bicarbonate solution. The organic phase was dried and evaporated and the residue was crystallized from ethyl acetate to yield yellowish product. The analytical sample was recrystallized from ethyl acetate/hexane, mp 216°–218° C.

EXAMPLE 16

7-Chloro-5-(2-fluorophenyl)-2,3-dihydro-1H-1,4-benzodiazepine-2-N'-hydroxy-N-methylcarboximidamide Reduction of 3.45 g (0.01 mole) of 7-chloro-5-(2-fluorophenyl)-3H-1,4-benzazepine-2-N'-hydroxy-N-methylcarboximidamide with 1 g (0.026 mole) of sodium borohydride in 100 ml of ethanol for 4 hours at room temperature gave, after the workup described above, end product, crystallized from ethyl acetate. The analytical sample was recrystallized from methanol/ethyl acetate, mp 215°–217° C. dec.

EXAMPLE 17

7-Chloro-5-(2-fluorophenyl)-2,3-dihydro-1H-1,4-benzodiazepine-2-N'-hydroxy-N,N-dimethylcarboximidamide This compound was similarly obtained by treatment of 7-chloro-5-(2-fluorophenyl)-3H-1,4-benzodiazepine-2-N'-hydroxy-N,N-dimethylcarboximidamide in ethanol/tetrahydrofuran with sodium borohydride for 4 hours at room temperature. The usual workup and crystallization from ether gave end product. For analysis it was recrystallized from methanol/ethyl acetate, mp 178°–180° C.

EXAMPLE 18

7-Chloro-5-(2-fluorophenyl)-2,3-dihydro-1H-1,4-benzodiazepine-4-oxide-2-N'-hydroxy-N,N-dimethylcarboximidamide Reduction of 7-chloro-5-(2-fluorophenyl)-3H-1,4-benzodiazepine-2-N'-hydroxy-N,N-dimethylcarboximidamide 4-oxide with sodium borohydride in ethanol for 3 hours at room temperature gave the end compound. For analysis it was recrystallized from ethyl acetate/ether, mp 145°–150° C. dec. (solvate with 1/6 mole of ether).

EXAMPLE 19

7-Chloro-5-(2-fluorophenyl)-2,3-dihydro-N-hydroxy-α-(1-pyrrolidinyl)-1H-1,4-benzodiazepine-2-methanimine This compound was similarly obtained by reduction of 7-chloro-5-(2-fluorophenyl)-2-[1-[(hydroxyimino)-methyl]pyrrolidinyl]-3H-1,4-benzodiazepine with sodium borohydride in ethanol/tetrahydrofuran. It was crystallized from ethanol/ether and recrystallized from tetrahydrofuran/ethanol to give off-white crystals with mp 200°–202° C. dec.

EXAMPLE 20

7-Chloro-5-(2-fluorophenyl)-2,3-dihydro-N-hydroxy-α-(1-pyrrolidinyl)-1H-1,4-benzodiazepine-2-methanimine 4-oxide Reduction of 2 g (5 mmole) of 7-chloro-5-(2-fluorophenyl)-2-[1-[(hydroxyimino)-methyl]pyrrolidinyl]-3H-1,4-benzodiazepine 4-oxide with 0.8 g sodium borohydride in 50 ml of ethanol and 25 ml of tetrahydrofuran (4 hours at room temperature) gave after the usual workup and crystallization from ethyl acetate the end product. For analysis it was recrystallized from methanol/ethyl acetate, mp 182°–183° C. dec.

EXAMPLE 21

7-Chloro-5-(2-fluorophenyl)-2,3-dihydro-N-hydroxy-α-(4-morpholinyl)-1H-1,4-benzodiazepine-2-methanimine This compound was obtained by reduction of 7-chloro-5-(2-fluorophenyl)-2-[4-[(hydroxyimino)methyl]morpholinyl]-3H-1,4-benzodiazepine with sodium borohydride in ethanol/tetrahydrofuran (4 hours at room temperature). It was crystallized from ether and recrystallized from methanol/ethyl acetate/hexane for analysis to give off-white needles with mp 133°–137° C.

EXAMPLE 22

7-Chloro-5-(2-fluorophenyl)-2,3-dihydro-N-hydroxy-α-(4-morpholinyl)-1H-1,4-benzodiazepine-2-methanimine 4-oxide Analogously, reduction of 7-chloro-5-(2-fluorophenyl)-2-[4-[(hydroxyimino)-methyl]morpholinyl]-3H-1,4-benzodiazepine 4-oxide gave the end compound. It was crystallized from ethyl acetate and recrystallized from methanol/ethyl acetate for analysis to leave light yellow crystals with mp 192°–193° C. dec.

EXAMPLE 23

8-Chloro-3-dimethylamino-6-(2-fluorophenyl)-4H-imidazo[1,5-a][1,4]benzodiazepine A mixture of 1.8 g (5 mmole) of 7-chloro-5-(2-fluorophenyl)-2,3-dihydro-1H-1,4-benzodiazepine-2-N'-hydroxy-N,N-dimethylcarboximidamide, 0.5 g (16.6 mmole) of paraformaldehydr, 0.1 g of p-toluene sulfonic acid hydrate and 100 ml of ethanol was heated to reflux for 5 hours. The solvent was evaporated under reduced pressure and the residue was partitioned between methylene chloride and aqueous sodium bicarbonate solution. The organic phase was dried and evaporated. Crystallization from ether/2-propanol gave end product which was purified by chromatography over 30 g of silica gel using 5% (v/v) of ethanol in methylene chloride. The analytical sample was recrystallized from ethyl acetate/hexane to give light yellow crystals with mp 161°–162° C.

The dihydrochloride of this compound was prepared by heating a solution in ethanol with excess ethanolic hydrogen chloride and crystallizing by addition of ether. The analytical sample was recrystallized from ethanol/ether and had mp 178°–182° C. dec.

EXAMPLE 24

8-Chloro-3-dimethylamino-6-(2-fluorophenyl)-4H-imidazo[1,5-a][1,4]benzodiazepine 5-oxide A mixture of 3.8 g (0.01 mole) of 7-chloro-5-(2-fluorophenyl)-2,3-dihydro-1H-1,4-benzodiazepine-4-oxide-2-N'-hydroxy-N,N-dimethylcarboximidamide, 1 g (0.033 mole) of paraformaldehyde, 0.3 g of p-toluene sulfonic acid hydrate and 150 ml of ethanol was heated to reflux for 20 hours. The solvent was evaporated under reduced pressure and the residue was partitioned between methylene chloride and sodium bicarbonate solution. The organic layer was dried and evaporated. Crystallization of the residue from ether/2-propanol gave end product as yellow crystals. The analytical sample was purified by chromatography over silica gel using 5% (v/v) of ethanol in methylene chloride and crystallized from ethyl acetate/hexane to give yellow crystals with mp 203°–206° C.

EXAMPLE 25

8-Chloro-6-(2-fluorophenyl)-3-pyrrolidinyl-4H-imidazo[1,5-a][1,4]benzodiazepine

A mixture of 1 g of 8-chloro-6-(2-fluorophenyl)-3-pyrolidinyl-4H-imidazo[1,5-a][1,4]benzodiazepine 5-oxide, 5 g of Raney nickel, 25 ml of tetrahydrofuran and 25 ml of ethanol was hydrogenated at atmospheric pressure for 15 hours. The catalyst was removed by filtration over Celite and the filtrate was evaporated. The residue was passed over silica gel using 5% (v/v) of ethanol in methylene chloride. Crystallization from ether/hexane gave end product as yellowish crystals with mp 114°–118° C.

EXAMPLE 26

8-Chloro-6-(2-fluorophenyl)-3-pyrolidinyl-4H-imidazo[1,5-a][1,4]benzodiazepine 5-oxide A mixture of 0.8 g (2 mmole) of 7-chloro-5-(2-fluorophenyl)-2,3-dihydro-N-hydroxy-α-(1-pyrrolidinyl)-1H-1,4-benzodazepine-2-methanimine 4-oxide, of 0.2 g of paraformaldehyde, 60 mg of p-toluene sulfonic acid and 25 ml of ethanol was heated to reflux for 8 hrs. The reaction mixture was worked up as described above and the residue was crystallized from ether and a small amount of 2-propanol to give end product. It was recrystallized from tetrahydrofuran/2-propanol for analysis to give light yellow crystals with mp 190°–192° C.

EXAMPLE 27

8-Chloro-6-(2-fluorophenyl)-3-morpholino-4H-imidazo[1,5-a][1,4]benzodiazepine 5-oxide A mixture of 3 g (7.1 mmole) of 7-chloro-5-(2-fluorophenyl)-2,3-dihydro-N-hydroxy-α-(4-morpholinyl)-1H-1,4-benzodiazepine-2-methanimine 4-oxide, 0.6 g (20 mmole) of paraformaldehyde, 100 ml of ethanol and 250 mg of paratoluene sulfonic acid hydrate was heated to reflux for 16 hours. The crude product obtained after the usual workup was chromatographed over 60 g of silica gel using 5% (v/v) of ethanol in methylene chloride for elution. The clean fractions of product were combined and evaporated. The residue was crystallized from ether and recrystallized from ethyl acetate/hexane for analysis to yield end product as yellow crystals with mp 200°–203° C.

EXAMPLE 28

8-Chloro-6-(2-fluorophenyl)-1-methyl-3-morpholino-4H-imidazo[1,5-a][1,4]benzodiazepine (A) A mixture of 1 g of 8-chloro-6-(2-fluorophenyl)-1-methyl-3-morpholino-4H-imidazo[1,5-a][1,4]benzodiazepine 5-oxide, 25 ml of tetrahydrofuran, 25 ml of ethanol and ca. 5 g of Raney nickel was stirred under an atmosphere of hydrogen for 15 hours. The catalyst was filtered off and the filtrate was evaporated. The residue was passed over a pad of silica gel using 5% (v/v) of ethanol in methylene chloride for elution. The eluates were evaporated and crystallized from ether/hexane to give end product as light yellow crystals with mp 173°–175° C. The analytical sample was recrystallized from ethyl acetate/hexane, mp 175°–177° C.

(B) A mixture of 0.4 g of 7-chloro-5-(2-fluorophenyl)-2,3-dihydro-N-hydroxy-α-(4-morpholinyl)-1H-1,4-benzodiazepine-2-methanimine, 5 ml of glacial acetic acid and 0.4 ml of acetaldehyde was heated to reflux for 5 minutes. The usual workup and chromatography of the crude reaction mixture on 5 g of silica gel using 5% (v/v) of ethanol in methylene chloride gave yellow crystalline product identical with that described above.

EXAMPLE 29

8-Chloro-6-(2-fluorophenyl)-1-methyl-3-morpholino-4H-imidazo[1,5-a][1,4]benzodiazepine 5-oxide A mixture of 4.2 g (0.01 mole) of 7-chloro-5-(2-fluorophenyl)-2,3-dihydro-N-hydroxy-α-(4-morpholinyl)-1H-1,4-benzodiazepine-2-methanimine 4-oxide, 50 ml of glacial acetic acid and 4 ml of acetaldehyde was heated to reflux for 5 minutes. The cooled reaction mixture was poured on ice, made alkaline with ammonia and extracted with methylene chloride. The extracts were dried and evaporated and the residue was crystallized from ether/2-propanol to yield yellow crystals.

For analysis the product was purified by passing over silica gel using 5% (v/v) of ethanol in methylene chloride and crystallized from ethyl acetate, mp 217°–220° C. dec.

EXAMPLE 30

8-Chloro-6-(2-fluorophenyl)-3-(4-methylpiperazinyl)-4H-imidazo[1,5-a][1,4]benzodiazepine 5-oxide A mixture of 4.3 g (0.01 mole) of [7-chloro-5-(2-fluorophenyl)-4-oxide-3H-1,4-benzodiazepin-2-yl](4-methyl-1-piperazinyl)methanone oxime, 200 ml of ethanol, 100 ml of tetrahydrofuran and 1.6 g of sodium borohydride was stirred at room temperature for 4 hours. The solvents were evaporated partially under reduced pressure and the residue was partitioned between methylene chloride and sodium bicarbonate solution. The organic phase was dried and evaporated. The crude product was converted to the hydrochloride by treatment with ethanolic hydrogen chloride to give yellow crystals. These crystals were reconverted to the base by partitioning between methylene chloride and sodium carbonate solution. The methylene chloride layer was dried and evaporated to leave resinous 7-chloro-5-(2-fluorophenyl)-2,3-dihydro-N-hydroxy-α-(4-morpholinyl)-1H-1,4-benzodiazepine-2-methanimine 4-oxide. This material was combined with 125 ml of ethanol, 0.8 g of paraformaldehyde and 0.4 g of paratoluene sulfonic acid hydrate. This mixture was heated to reflux for 48 hours and was then evaporated. The residue was partitioned between methylene chloride and sodium carbonate solution. The organic layer was dried and evaporated. Crystallization of the dark residue from ether containing a small amount of 2-propanol yielded end product as yellow crystals. For analysis a sample was purified by passing over silica gel using methylene chloride/methanol 1:1 (v/v) and by crystallizing from ethyl acetate/ether to give light yellow crystals with mp 184°–186° C.

EXAMPLE 31

7-Chloro-5-(2-fluorophenyl)-N-hydroxy-α-nitro-3H-1,4-benzodiazepine-2-methanimine Sodium nitrite, 5 g (0.072 mole), was added in portions over a period of 5 min to a solution of 20 g (0.06 mole) of 7-chloro-1,3-dihydro-5-(2-fluorophenyl)-2-nitromethylene-2H-1,4-benzodiazepine* in 100 ml of glacial acetic acid. Following the addition, the reaction mixture was stirred at room temperature for 15 min. The product, which crystallized partially during this period, was further precipitated by slow addition of 50 ml of water and collected by filtration. The crystals were washed with water, sucked dry and washed with methanol/ether to leave light yellow product. The filtrate was diluted with water and extracted with methylene chloride. The extracts were washed with water, dried and evaporated. Crystallization of the residue from methylene chloride/hexane yielded additional product. The analytical sample was recrystallized from ether to give pale yellow crystals with mp 220°–230° C. dec.

*Walser et al., *J. Org. Chem.* 43, 936 (1978)

EXAMPLE 32

7-Chloro-5-(2-fluorophenyl)-N-hydroxy-α-nitro-3H-1,4-benzodiazepine-2-methanimine 4-oxide 7-Chloro-5-(2-fluorophenyl)-1,3-dihydro-2-nitromethylene-2H-1,4-benzodiazepine-4-oxide* 7 g (0.02 mole), was dissolved by heating in 250 ml of glacial acetic acid. The solution was cooled with tap water and when the temperature reached 70° C. the addition of 1.9 g (0.0275 mole) of sodium nitrite was started. The sodium nitrite was added over a period of 10 min while cooling was continued. Following the addition, the mixture was stirred for 1½ hr at room temperature, diluted with water and extracted with methylene chloride. The extracts were washed with water, dried over sodium sulfate and evaporated. Crystallization of the residue from ethyl acetate yielded yellow crystals.

EXAMPLE 33

7-Chloro-5-(2-fluorophenyl)-N-methoxy-α-nitro-3H-1,4-benzodiazepine-2-methanimine 4-oxide A solution of diazomethane in ether was added to a suspension of 3.8 g (0.01 mol) of 7-chloro-5-(2-fluorophenyl)-N-hydroxy-α-nitro-3H-1,4-benzodiazepine-2-methanimine 4-oxide in 200 ml of methylene chloride. The mixture was stirred for 1 hr at room temperature whereby a clear solution resulted. The excess diazomethane was destroyed by addition of acetic acid. The reaction mixture was washed with aqueous sodium bicarbonate solution, dried over sodium sulfate and evaporated. Crystallization of the residue from ether yielded yellow crystals. The analytical sample was recrystallized from ether, mp 207°–209°.

EXAMPLE 34

7-Chloro-5-(2-fluorophenyl)-2-{[4-methoxyimino)methyl]morpholinyl}-3H-1,4-benzodiazepine 4-oxide A mixture of 3.9 g (0.01 mol) of 7-chloro-5-(2-fluorophenyl)-N-methoxy-α-nitro-3H-1,4-benzodiazepine-2-methanimine 4-oxide, 100 ml of tetrahydrofuran and 5 ml of morpholine was allowed to stand at room temperature for 2 hrs. After partial evaporation under reduced pressure, the reaction mixture was partitioned between methylene chloride and aqueous sodium bicarbonate solution. The organic phase was dried and evaporated and the residue was crystallized from ether/hexane to yield yellow crystals with mp 170°–173° C. The analytical sample was recrystallized from the same solvents.

EXAMPLE 35

8-Chloro-6-(2-fluorophenyl)1-methyl-3-morpholino-4H-imidazo[1,5-a][1,4]benzodiazepine 5-oxide A mixture of 215 mg of 7-chloro-5-(2-fluorophenyl)-2-{[4,-(methoxyimino)methyl]-morpholinyl}-3H-1,4-benzoidazepine 4-oxide, 5 ml of ethanol, 5 ml of tetrahydrofuran and 0.2 g sodium borohydride was stirred at room temperature for 4 hrs. After partitioning between methylene chloride and aqueous sodium bicarbonate solution, the organic layer was dried and evaporated to leave crude 8-chloro-6-(2-fluorophenyl)-2,3-dihydro-2-[4-(methoxyimino)methyl]morpholinyl-1H-1,4-benzodiazepine 4-oxide which was dissolved in 5 ml of glacial acetic acid. Following the addition of 0.2 ml of acetaldehyde, the solution was heated to reflux for 2 min. Then it was poured on ice, made alkaline with ammonia and extracted with methylene chloride/ether. The organic layer was dried and evaporated. Crystallization of the residue from ethyl acetate gave end product with mp 217°–220° C. dec.

EXAMPLE 36

8-Chloro-6-(2-fluorophenyl)-1-methyl-3-morpholino-4H-imidazo[1,5-a][1,4]benzodiazepine A mixture of 0.2 g of 8-chloro-6-(2-fluorophenyl)-1-methyl-3-morpholino-4H-imidazo[1,5-a][1,4]-benzodiazepine 5-oxide, 0.2 ml of hexachlorodisilane and 10 ml of methylene chloride was allowed to sit for two days. It was then diluted with toluene and washed with 1 N sodium hydroxide solution. The organic phase was dried and evaporated. Crystallization of the residue from ether/hexane gave end product with mp 172°–174° C.

EXAMPLE 37

7-Chloro-5-(2-fluorophenyl)-2-[4-(methoxyimino)methyl]-morpholinyl-3H-1,4-benzodiazepine Morpholine, 1 ml, was added to a solution of 0.5 g of 7-chloro-5-(2-fluorophenyl)-N-methoxy-α-nitro-3H-1,4-benzodiazepine-2-methanimine in 10 ml of tetrahydrofuran. After standing at room temperature for 3 hrs, the solvent was evaporated and the residue was partitioned between methylene chloride and aqueous sodium bicarbonate solution. The organic layer was dried and evaporated. Crystallization of the residue from ether/hexane yielded end product with mp 141°–143° C.

EXAMPLE 38

7-Chloro-5-(2-fluorophenyl)-2,3-dihydro-2-{[(methoxyimino)methyl]aziridinyl}-1H-1,4-benzodiazepine 4-oxide A mixture of 2 g of 7-chloro-5-(2-fluorophenyl)-N-methoxy-α-nitro-3H-1,4-benzodiazepine-2-methanimine 4-oxide, 30 ml of tetrahydrofuran and 2 ml of aziridine was allowed to stand at room temperature for 1 hr. After partitioning between methylene chloride and aqueous sodium bicarbonate solution, the organic phase was dried and evaporated to leave crude 7-chloro-5-(2-fluorophenyl)-2-{[(methoxyimino)methyl]-aziridinyl}-3H-1,4-benzodiazepine 4-oxide.

This material was dissolved in a mixture of 30 ml of ethanol and 30 ml of tetrahydrofuran. After addition of 1 g of sodium borohydride, the solution was stirred for 4 hrs at room temperature and partitioned between methylene chloride and water. The organic layer was dried and evaporated. Crystallization of the residue from ether gave yellowish crystals with mp 161°–164° C. The analytical sample was recrystallized from ethyl acetate/hexane.

What is claimed

1. A process to produce a compound of the formula wherein X is selected from the group consisting of hydrogen, halogen, nitro and trifluoromethyl; Y is selected from the group consisting of hydrogen, halogen or trifluoromethyl; $R_1$ is hydrogen or lower alkyl and $R_2$ is diloweralkylamino, dibenzylamino or morpholino which comprises A. reacting a compound of the formula

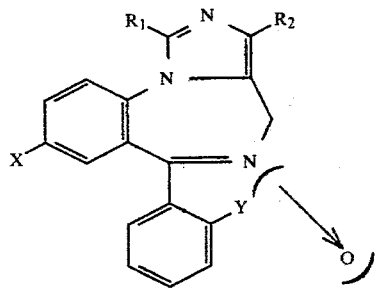

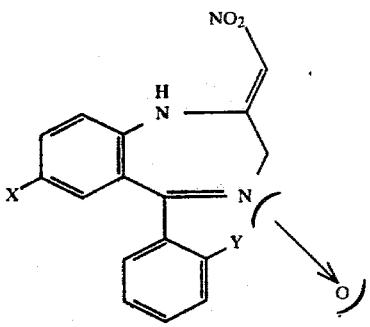

wherein X and Y are as above with a nitrosating agent,

B. alkylating the product of (A) by reaction with diazomethane or diazoethane,

C. nucelophilically displacing the nitro group of the product of (A) or (B) with ammonia, a primary or secondary amine or an alkali metal salt of a primary or secondary amine, D. reacting the product of (C) with sodium borohydride, E. reacting the product of (D) with formaldehyde or acetaldehyde in the presence of an acid catalyst.

* * * * *